United States Patent
Snell et al.

(10) Patent No.: US 7,647,104 B1
(45) Date of Patent: Jan. 12, 2010

(54) ISCHEMIA DETECTION USING PACED DEPOLARIZATION INTEGRAL AND INTRACARDIAC ELECTROGRAM TEMPLATE COMPARISON

(75) Inventors: Jay Snell, Studio City, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 337 days.

(21) Appl. No.: 11/549,517

(22) Filed: Oct. 13, 2006

(51) Int. Cl.
*A61N 1/362* (2006.01)

(52) U.S. Cl. .......................................... 607/9; 600/510

(58) Field of Classification Search ......... 600/508–510; 607/14, 9, 17
See application file for complete search history.

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,940,052 A | 7/1990 | Mann et al. |
| 4,944,298 A | 7/1990 | Sholder |
| 5,466,254 A | 11/1995 | Helland |
| 5,476,483 A | 12/1995 | Bornzin et al. |
| 6,021,350 A | 2/2000 | Mathson |
| 6,377,852 B1 | 4/2002 | Bornzin et al. |
| 2003/0050671 A1* | 3/2003 | Bradley ..................... 607/27 |
| 2003/0060854 A1 | 3/2003 | Zhu |
| 2004/0088017 A1* | 5/2004 | Sharma et al. ............. 607/25 |

FOREIGN PATENT DOCUMENTS

WO          0326740 A1     4/2003

OTHER PUBLICATIONS

Theres, Heinz P. et al., "Detection of Acute Myocardial Ischemia During Percutaneous Transluminal Coronary Angioplasty by Endocardial Acceleration,".

* cited by examiner

*Primary Examiner*—George R Evanisko

(57) ABSTRACT

A method and apparatus for analyzing IEGM waveforms is disclosed. The method includes generating a long term ensemble average of a plurality of baseline IEGM waveforms and generating a short term ensemble average of at least a portion of the plurality of baseline IEGM waveforms. The method further includes determining a short term absolute point value as a function of the absolute value of the difference of the amplitude of the short term ensemble average and a test IEGM waveform and a long term absolute point value as a function of the difference of the amplitude of the long term ensemble average and the test waveform at a plurality of sample points. The disclosed method further includes detecting ischemia if the difference between the short term absolute point value and the long term absolute point value is greater than an ischemia detection threshold.

15 Claims, 7 Drawing Sheets

ISCHEMIA DETECTION USING PACED DEPOLARIZATION INTEGRAL AND INTRACARDIAC ELECTROGRAM TEMPLATE COMPARISON

FIELD OF THE INVENTION

The invention relates to implantable medical devices and more particularly to implantable cardiac stimulation devices.

BACKGROUND

Implantable cardiac stimulation devices are now commonly used in medical practice. These devices provide periodic electrical stimulus to the heart to regulate heart function. For example, a pacemaker is generally arranged to deliver rhythmic electrical pulses to the heart to maintain a normal rhythm in patients having bradycardia or other conduction abnormalities. In addition, an implantable cardioverter defibrillator, commonly referred to as an "ICD", can also recognize tachycardia and/or fibrillation and deliver electrical therapy to terminate such arrhythmias.

Various implantable devices, i.e. cardiac pacemakers or cardiovertors, have been developed to analyze intracardiac electrograms to diagnose the presence of conduction abnormalities as well as the presence and the evolution of various disease states in real time, so as to be able to adapt consequently the operation of the device. An intracardiac electrogram (IEGM) signal collected (i.e. sensed or detected) by electrodes coupled to one or more leads implanted in a patient's heart can be used to monitor a series of wave complexes known as the "PQRST" complexes corresponding to the succession of the cardiac beats of the patient. The QRS complex in a cardiac cycle represents the depolarization of the ventricles and is followed by a T wave which represents the repolarization of the ventricles.

The T wave (repolarization wave) amplitude and shape are quite variable, and are sensitive to conduction disturbances in the myocardium and are therefore, often used to detect and monitor the progression of various disease states such as ischemia. For example, elevation of the amplitude of the T-wave (the ST segment) is a significant indicator of cardiac electric instability of the patient. The level of amplitude elevation of the ST segment can therefore be used to detect and monitor the progression of ischemia. However, the ST segment can be affected by conditions other than ischemia, such as electrolyte imbalance, mental stress, diabetes and the like, reducing the efficacy of ST segment analysis.

Similarly, fusion beats can corrupt IEGM analysis, further reducing the efficacy of rhythm analysis and detection of disease progression. Fusion is a variable and essentially random event that results from a cardiac depolarization that originates from more than one cardiac focus, one of which is a pacing pulse and the other(s) is(are) intrinsic in origin. An algorithm that evaluates or processes signals during cardiac repolarization can be negatively affected by 'fusion' due to the chaotic nature of the resulting waveform that results from a fusion beat. Thus, such 'fusion' events should be censored from analysis, and excluded from rhythm analysis and disease state detection.

SUMMARY

In accordance with one aspect of the present invention, a method for operating a medical device includes generating a baseline IEGM template and determining the absolute value of the difference of the amplitude of a test IEGM complex and the amplitude of the baseline IEGM template at a plurality of sample points. This aspect of the present invention further includes detecting a fusion beat if a sum of the differences at the plurality of sample points is greater than a fusion detection threshold.

In a further aspect of the present invention a method for operating a medical device includes generating a long term ensemble average of a plurality of baseline IEGM waveforms and generating a short term ensemble average of at least a portion of the plurality of baseline IEGM waveforms. This aspect of the present invention further includes determining the absolute value of the difference of the amplitude of the short term ensemble average and a test IEGM waveform and the amplitude of the long term ensemble average and the test waveform at a plurality of sample points and detecting ischemia if a sum of the differences at the plurality of sample points is greater than an ischemia detection threshold.

In a further aspect of the present invention a medical device includes a pulse generator adapted to deliver a plurality of pacing pulses to a patient's heart and a sensing circuit adapted to sense IEGM waveforms. This aspect of the present invention further includes a microcontroller adapted to determine a long term ensemble average of a plurality of baseline IEGM waveforms and short term ensemble average of at least a portion of the plurality of baseline IEGM waveforms. In this aspect of the present invention the microcontroller is further adapted to determine the absolute value of the difference between a long term ensemble average and a test IEGM waveform and a short term ensemble average and the test IEGM waveform at a plurality of sample points and to detect ischemia if a sum of the differences at the plurality of sample points is greater than an ischemia detection threshold.

BRIEF DESCRIPTION OF THE DRAWINGS

Further features and advantages may be more readily understood by reference to the following description taken in conjunction with the accompanying drawings, in which.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

In one embodiment of the present invention an implantable stimulation device monitors the morphology of the QRS wave to detect ischemia. The present invention may be implemented in connection with any stimulation device that is configured or configurable to monitor intrinsic electrical cardiac activity. However, the advantages of the present invention may be best understood in connection with an exemplary stimulation device that is capable of being used in connection with the various embodiments that are described below.

It is to be appreciated and understood that other stimulation devices, including those that are not necessarily implantable, can be used and that the description below is given, in its specific context, to assist the reader in understanding, with more clarity, the inventive embodiments described herein. In the description that follows, like numerals or reference designators will be used to refer to like parts or elements throughout.

Figure 1:
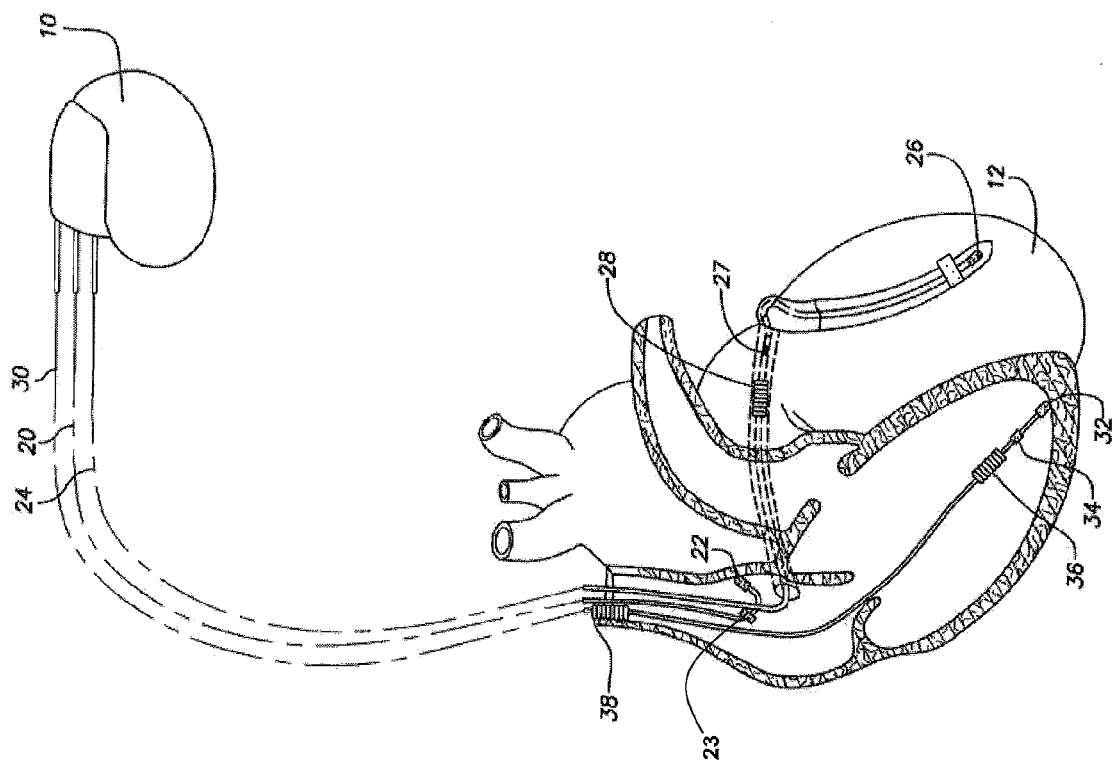
FIG. 1 is a simplified diagram of one embodiment of an implantable stimulation device in electrical communication with a patient's heart for delivering multi-chamber stimulation and shock therapy in accordance with one embodiment of the invention.

FIG. 1 illustrates a prophylactic defibrillation and stimulation device 10 (also referred to herein as a prophylactic pacer/defibrillator) in electrical communication with a heart 12 by way of three leads 20, 24 and 30, suitable for delivering multi-chamber pacing stimulation therapy and ventricular defibrillation shock therapy. To sense atrial cardiac signals and to provide right atrial chamber stimulation therapy, device 10 is coupled to an implantable right atrial lead 20 having at least an atrial tip electrode 22 and an atrial ring electrode 23, which typically is implanted in the right atrial appendage.

To sense left atrial and ventricular cardiac signals and to provide left chamber pacing therapy, stimulation device 10 is coupled to a coronary sinus lead 24 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 10 is also shown in electrical communication with the patient's heart 12 by way of an implantable right ventricular lead 30 having, in this implementation, a right ventricular tip electrode 32, a right ventricular ring electrode 34, a right ventricular (RV) coil electrode 36 (or other electrode capable of delivering a shock), and superior vena cava (SVC) coil electrode 38 (or other electrode capable of delivering a shock). Typically, the right ventricular lead 30 is transvenously inserted into the heart 12 to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of sensing or receiving cardiac signals, and delivering stimulation in the form of pacing and shock therapy to the right ventricle.

Figure 2:
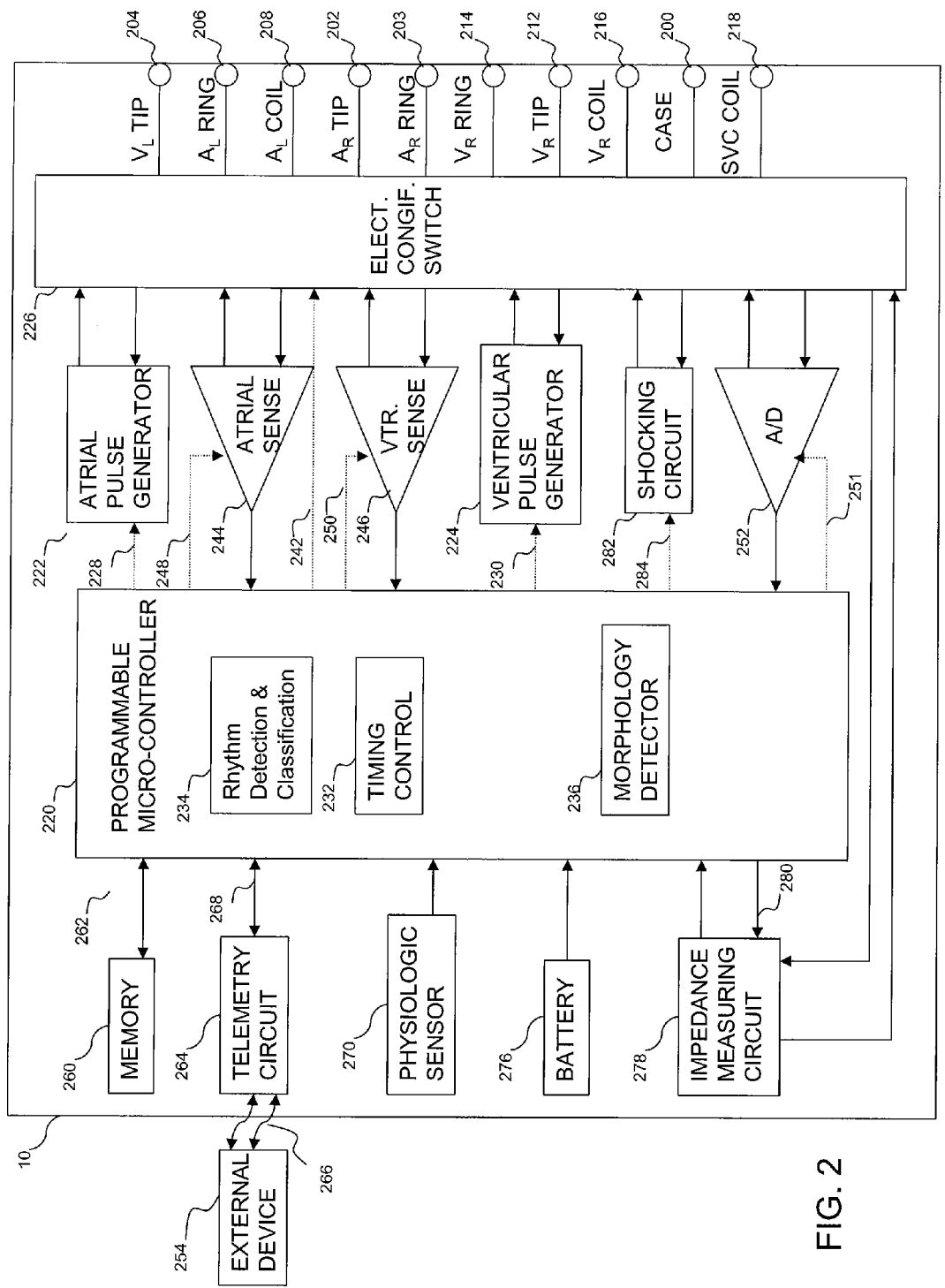
FIG. 2 is a simplified block diagram of a multi-chamber implantable stimulation device configured to provide cardioversion, defibrillation or pacing stimulation or any combination thereof in accordance with one embodiment of the invention.

FIG. 2 shows an exemplary, simplified block diagram depicting various components of stimulation device 10. The stimulation device 10 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be selected to act as the return electrode for all "unipolar" modes. Housing 200 may further be used as a return electrode alone or in combination with one or more of the coil electrodes 28, 36 or 38 for shocking purposes. Housing 200 further includes a connector (not shown) having a plurality of terminals 202, 203, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 22. A right atrial ring terminal (AR RING) 203 may also be included adapted for connection to the atrial ring electrode 23. To achieve left chamber sensing, pacing, and shocking, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 26, the left atrial ring electrode 27, and the left atrial coil electrode 28, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry.

Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 20, the coronary sinus lead 24, and/or the right ventricular lead 30 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The microcontroller 220 is further coupled to a memory 260 by a suitable data/address bus 262, wherein the programmable operating parameters used by the microcontroller 220 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 10 may be non-invasively programmed into the memory 260 through a telemetry circuit 264 in telemetric communication via communication link 266 with an external device 254, such as a programmer, trans-telephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 10 (as contained in the microcontroller 220 or memory 260) to be sent to the external device 254 through an established communication link 266.

The stimulation device 10 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 10, it is to be understood that the physiologic sensor 270 may also be external to the stimulation device 10, yet still be implanted within or carried by the patient.

Examples of physiologic sensors that may be implemented in device 10 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 10, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 10 may employ lithium/silver vanadium oxide batteries.

The stimulation device 10 can further include magnet detection circuitry (not shown), coupled to the microcontroller 220, to detect when a magnet is placed over the stimulation device 10. A magnet may be used by a clinician to perform various test functions of the stimulation device 10 and/or to signal the microcontroller 220 that the external programmer 254 is in place to receive or transmit data to the microcontroller 220 through the telemetry circuits 264.

The stimulation device 10 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 20, the coronary sinus lead 24, and the right ventricular lead 30 through the switch 226 to sample cardiac signals across any pair of desired electrodes.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 20, coronary sinus lead 24, and the right ventricular lead 30, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations.

The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 10 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia.

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

In the case where the stimulation device 10 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220.

Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 200 may act as an active electrode in combination with the RV coil electrode 36, and/or as part of a split electrical vector using the SVC coil electrode 38 or the left atrial coil electrode 28 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 10 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The microcontroller 220 is further adapted to analyze the digitized intracardiac electrogram signals output by the data acquisition system to detect fusion beats. In one embodiment the microcontroller compares the digitized intracardiac electrogram signals to a baseline template stored in the implanted device to detect a fusion beat.

The occurrence of a fusion beat alters the depolarization and repolarization characteristics of the heart. As a result, the magnitude and shape of the evoked response measured within the ventricles differs from that of a "true" evoked response, i.e. an evoked response that otherwise would have occurred in response to just the V-pulse. Typically, the magnitude of the measured evoked response due to fusion is less than the true evoked response. In any case, the measure evoked response cannot be reliably used for the purposes of tracking various disease states or, typically, for most other purpose.

Therefore, one embodiment of the present invention monitors digitized intracardiac electrograms to detect changes in the morphology of the IEGM waveform to identify fusion beats. In this embodiment the magnitude of the change in the IEGM waveform is indicative of the likelihood of occurrence of a fusion beat.

Figure 3:
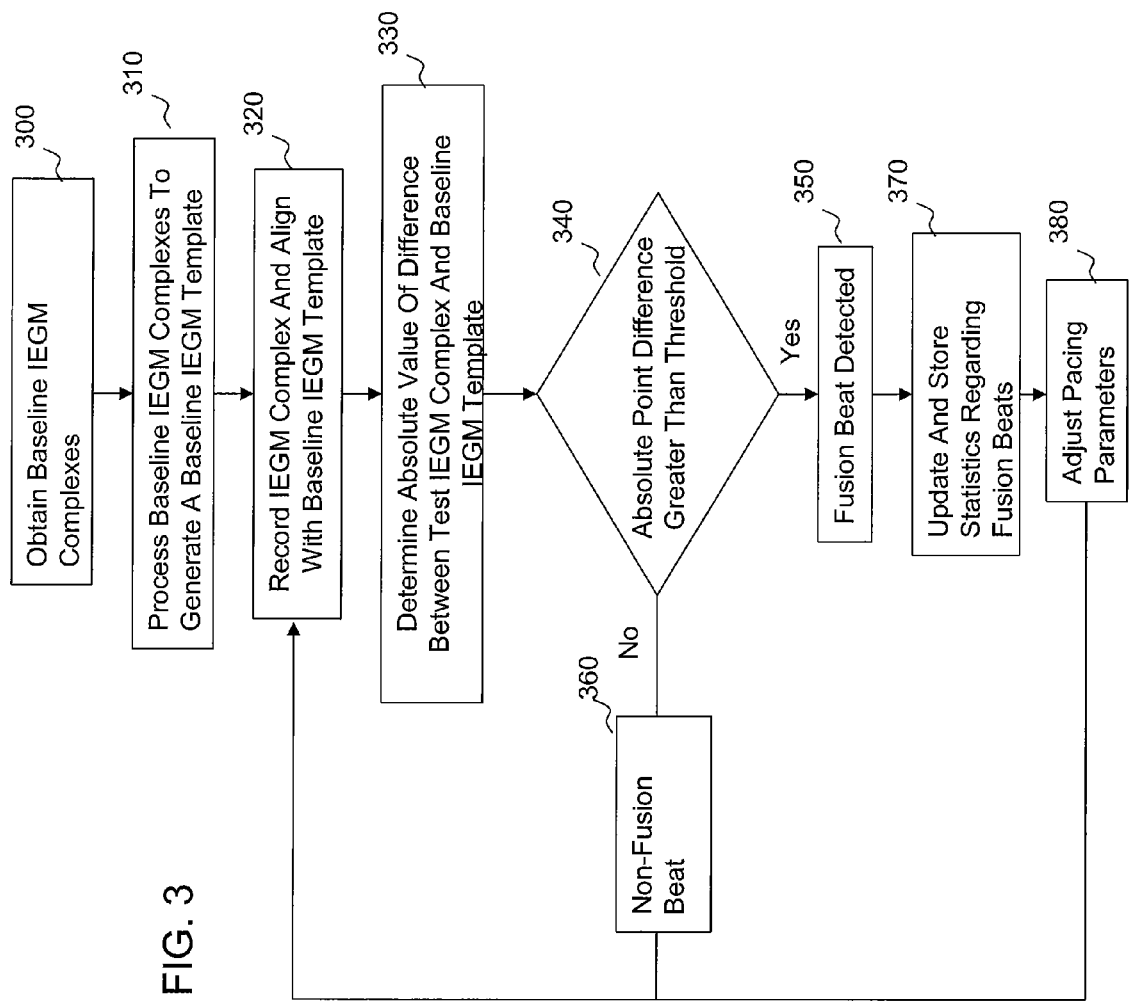
FIG. 3 is a flow chart illustrating operation of the implantable device of FIG. 2 in accordance with one embodiment of the invention.

For example, FIG. 3 is a flowchart illustrating the operation of one embodiment of a stimulation device to detect a fusion beat as a function of changes in the amplitude of the voltage of the IEGM waveform. In this flow chart, the various operational steps are summarized in individual "blocks". Such blocks describe specific actions or decisions that are carried out during operation of the illustrated device 10. Where a microcontroller (or equivalent) is employed, the flow chart presented herein provides the basis for a "control program" that may be used by such a microcontroller (or equivalent) to effectuate the desired control of the stimulation device.

In one embodiment of the present invention the microcontroller analyzes features of intracardiac electrograms (IEGMs) to monitor and or detect fusion beats. For example, in one embodiment the microcontroller analyzes the S-T segment of a measured IEGM, the measured T-wave and/or the unipolar paced evoked response to differentiate fusion beats from paced beats that have not combined with normally conducted intrinsic events.

In one embodiment of the present invention the microcontroller, either automatically or under the control of the treating physician, records a plurality of digitized baseline (non-ischemic) IEGM waveforms 300. The microcontroller then employs any one of a variety of digital signal processing techniques to generate an IEGM template from the digitized baseline waveforms.

In one embodiment the complexes are typically recorded for a pre-determined time period beyond the onset of the Q-wave. The microcontroller then uses any of a variety of processing techniques to align the recorded waveforms and generate a baseline template. For example, in some embodiments the microcontroller aligns the maximum amplitude points of the recorded complexes and calculates an ensemble average of the time sampled complexes to generate a baseline IEGM template that is stored in memory 310 for subsequent comparison purposes.

In some embodiments, fusion beats are not excluded from the generation of the IEGM template through ensemble averaging because the fusion beats are typically random in nature and thus tend to average out of the ensemble average. However, if the occurrence of fusion beats is persistent and consistent the IEGM template can be corrupted. In this instance the average deviation of the ensemble average will be large due to the consistent occurrence of fusion beats. Therefore, in some embodiments the microcontroller calculates the average deviation of the ensemble average to qualify the use of the ensemble average as an IEGM baseline template.

One of skill in the art will appreciate that ensemble averaging is just one of a variety of methods that may be used to generate a baseline IEGM template. Other methods could also be used to generate a baseline IEGM template.

In operation the micro-controller then monitors the evoked response of paced ventricular events by recording a digitized paced ventricular depolarization (e.g. IEGM complex) for comparison to the stored baseline IEGM template. In one embodiment the microcontroller aligns the maximum amplitude of the baseline IEGM template with the maximum amplitude of the IEGM complex under test 320. Alternatively, the microcontroller may record a plurality of consecutive or nearly consecutive IEGM complexes and ensemble average the recorded plurality of test complexes which is then used in the comparison test.

The implantable device then determines, by way of example, the absolute value of the difference between the amplitude at each point of the IEGM baseline template and each of the corresponding points of the digitized IEGM complex under test. In one embodiment the microcontroller then sums each of the difference values to determine the absolute point difference of the IEGM complex under test as compared to the baseline template 330. A small value for the absolute point difference indicates that the complex under test is close to the IEGM baseline template.

Therefore, in one embodiment the implantable device compares the absolute point difference between the complex under test and the baseline IEGM template to a threshold value to determine if the complex under test is a fusion beat 340. In this embodiment if the absolute point difference is greater than or equal to the threshold the IEGM complex under test is classified as a fusion beat 350. The present application can therefore be utilized to detect fusion beats for purposes of disqualifying any ectopic or aberrantly conducted heartbeat during evaluation of IEGM waveforms for any of a variety of applications.

Otherwise the waveform is classified as a non-fusion beat 360 and the device returns to monitoring IEGM waveforms. In one embodiment the implantable device tracks the percentage of fusion beats 370 and in some embodiments adjusts the pacing parameters 380 if the percentage of fusion beats exceeds a threshold value.

The microcontroller 220 is further adapted to analyze the digitized intracardiac electrogram signals output by the data acquisition system to detect the onset or evolution (i.e. progression or regression) of ischemia. In one embodiment the microcontroller compares the digitized intracardiac electrogram signals to a baseline template stored in the implanted device to detect myocardial ischemia.

Typically, IEGM waveforms are relatively stable during normal intrinsic events and non-fusion paced cycles. The onset and or evolution of an ischemic condition alters the depolarization and repolarization characteristics of the heart. For example, an ischemic region in the ventricle of the heart slows down the propagation of the excitation wave through the ventricles and is evidenced by changes in the IEGM waveform which models excitation wave propagation through the heart.

Changes in the IEGM waveform can also be affected by a number of other factors including but not limited to the IEGM recording vector, the location and magnitude of the ischemia, and the presence or absence of prior cardiac damage. An ischemic event typically results in a changed, but stable IEGM morphology relatively shortly after the onset of the ischemic condition.

Therefore, one embodiment of the present invention monitors digitized intracardiac electrograms to detect changes in the morphology of the IEGM waveform to identify the onset of an ischemic condition. In this embodiment the change in the IEGM waveform is proportional to the severity of the ischemia.

Figure 4:
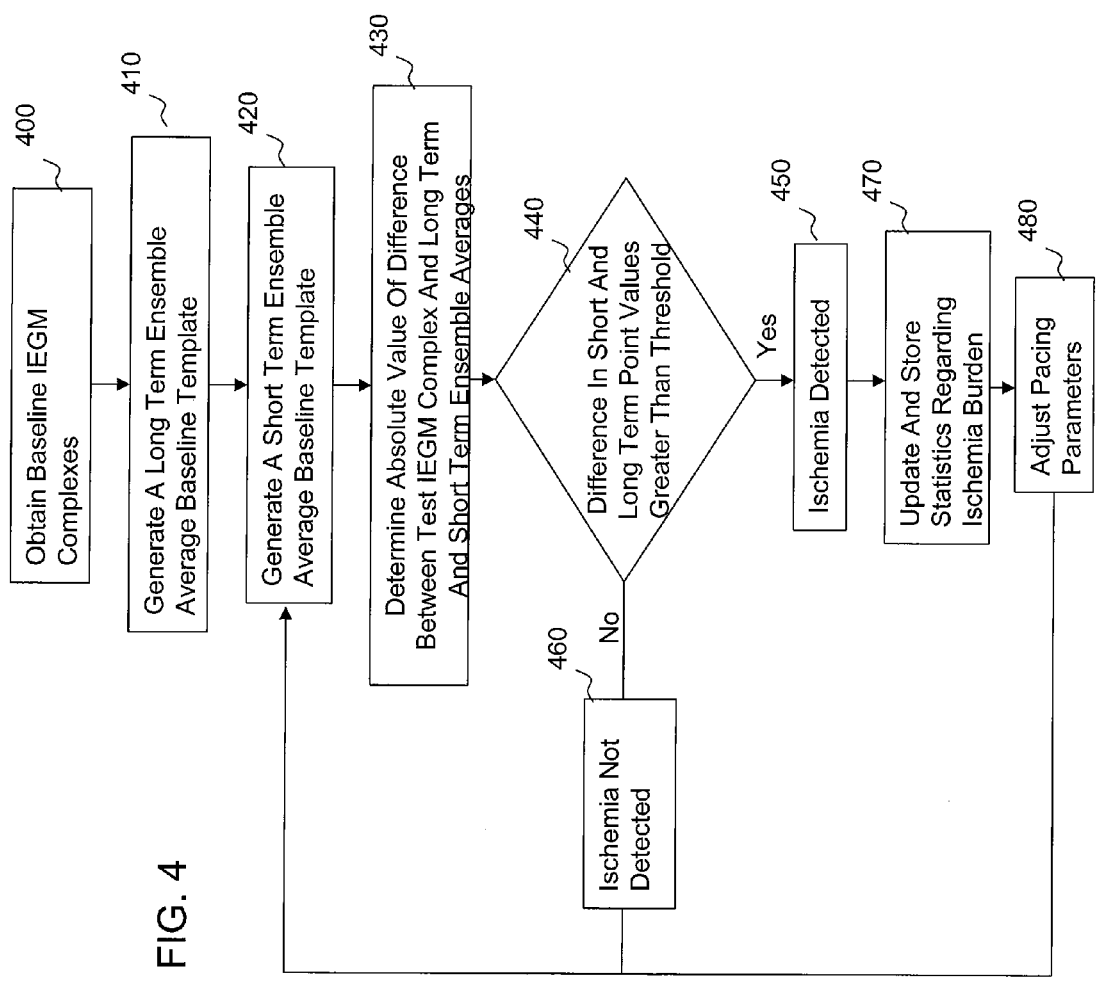
FIG. 4 is a flow chart illustrating operation of the implantable device of FIG. 2 in accordance with one embodiment of the invention.

For example, FIG. 4 is a flowchart illustrating the operation of one embodiment of a stimulation device to detect the onset or progression of ischemia as a function of changes in the amplitude of the voltage of the IEGM waveform. For example, in some embodiments the microcontroller analyzes the S-T segment of a measured IEGM, the measured T-wave and/or the unipolar paced evoked response to detect and or monitor the progression of ischemia.

In one embodiment of the present invention the microcontroller, either automatically or under the control of the treating physician, records a plurality of digitized baseline (non-ischemic) IEGM waveforms 400. The microcontroller then employs any one of a variety digital signal processing techniques to again generate an IEGM template from the digitized baseline waveforms.

In one embodiment the complexes are typically recorded for a pre-determined time period beyond the onset of the Q-wave. In some embodiments the microcontroller aligns the maximum amplitude points of the recorded complexes and calculates a long term ensemble average of the time sampled complexes to generate a baseline long term ensemble average template that is stored in memory 410 for subsequent comparison purposes. In this embodiment the long term ensemble average is calculated using a relatively long time constant to average out the effects of noise and fusion.

For example, in one embodiment the microcontroller periodically updates a running long term ensemble average. In other embodiments the microcontroller adds data to the ensemble average each time the device detects an evoked response. The microcontroller adds new data to the running ensemble average on a point by point basis using a running average for each data point.

In one embodiment the running long term ensemble average is calculated by first reducing the amplitude of each data point in the running average by a predetermined factor such as, for example, $1/256$ of its present value. One of skill in the art will appreciate that the scale factor for the long term ensemble average is not limited to a particular value but may be any of a range of values as programmed by the physician or as automatically determined by the device.

The running average is then updated for a current complex by scaling the amplitude of each data point in the current complex by the same predetermined factor. The microcontroller then adds the scaled values as illustrated below in EQ. (1) for an ensemble average consisting of 25 points:

$$EA(x)_n = EA(x)_{n-1} - (EA(x)_{n-1}/256) + (DATA(x)_n/256) \quad \text{EQ. (1)}$$

For x=1 to 25

In one embodiment of the present invention the implanted device also maintains a running short term ensemble average with a relatively short time constant that is more sensitive to morphological changes in the IEGM 420. For example, in one embodiment the running short term ensemble average is calculated by first reducing the amplitude of each data point in the running short term average by a predetermined factor such as, for example, $1/16$ of its present value.

One of skill in the art will appreciate that the scale factor for the short term ensemble average is not limited to a particular value but may be any of a range of values as programmed by the physician or as automatically determined by the device. Typically the scale factor will be chosen so that the short term ensemble average converges to a new morphology more quickly than the long term average in response to the occurrence of an ischemic event.

The running short term average is then updated for a current complex by scaling the amplitude of each data point in the current complex by the same predetermined factor. The microcontroller then adds the scaled values as illustrated below in EQ. (2) for an ensemble average consisting of 25 points:

$$EA(x)_n = EA(x)_{n-1} - (EA(x)_{n-1}/16) + (DATA(x)_n/16) \quad \text{EQ. (2)}$$

For x=1 to 25

In operation the micro-controller then periodically performs an ischemia test by digitizing a ventricular depolarization (e.g. a paced IEGM complex) for comparison to the stored long term and short term ensemble averages on a point by point basis. In one embodiment the microcontroller aligns the maximum amplitude of the complex under test with the maximum amplitude of the long term and short term ensemble average templates.

The implantable device then determines, by way of example, the absolute value of the difference between the amplitude of the voltage at each point of the long term ensemble average template and each of the corresponding points of the digitized IEGM complex under test. In this embodiment the implantable device also determines the absolute value of the difference between the amplitude of the voltage at each point of the short term ensemble average template and each of the corresponding points of the digitized IEGM complex under test 430. In one embodiment the microcontroller then sums each of the difference values to determine the absolute point difference of the IEGM complex under test and both the long term and short term ensemble average templates (i.e. the long term and short term absolute point differences).

In operation, the short term ensemble average, with a short time constant, converges relatively quickly to a new morphology in response to changes in an IEGM complex that result from the onset or progression of ischemia. The long term ensemble average, with a relatively long time constant, on the other hand does not converge quickly to a new morphology in response to changes in the most recent IEGM complexes.

Therefore, the value of the absolute point difference obtained from comparing an IEGM complex measured subsequent to the onset of ischemia to the short term ensemble average will be smaller than the value of the absolute point difference obtained from comparison to the long term ensemble average. When the divergence of these two absolute point difference values exceeds a defined threshold an ischemic event is detected.

Accordingly, in one embodiment the implantable device determines the difference between the short term absolute point difference and the long term absolute point difference 440 for a complex under test. In this embodiment the microcontroller detects an ischemic event if the difference between the values of the short term and long term absolute point differences is greater than or equal to a threshold value 450. Otherwise, ischemia is not detected 460 and the device reverts back to monitoring IEGM complexes.

In some embodiments the microcontroller calculates various statistics, such as, by way of example, the statistical mean, variance and the like, of the difference in the absolute point difference between the long term and short term ensemble averages and compares the mean or variance to a threshold to detect the onset of ischemia. The ischemia detection threshold is, by way of example, programmable and may vary depending upon the application, patient condition and physician preference. Further the interval at which ischemia diagnoses are performed also depends on the application.

For example, in some embodiments the microcontroller measures the ischemia burden approximately every one to two hours to generate a long-term diagnostic record. A long-term record of the patient's ischemia burden obtained through continuous monitoring is a useful adjunct to current methods of ischemia detection and diagnosis. Such a record may reveal infrequent or un-provokable ischemia perhaps associated with nascent coronary artery disease, vasospasm or embolism as well as trends in the progression or regression of coronary artery disease. A long-term record of ischemia burden can also be used to gauge the efficacy of, and/or patient compliance with, a course medication.

Therefore, in one embodiment, the microcontroller generates an ischemia burden metric for tracking the evolution of the ischemia 470. The burden metric in one embodiment is the ratio of periodic measurements for which ischemia is indicted relative to the total number of periodic measurements. In this embodiment the microcontroller stores and updates the ischemia burden, and any other clinically significant event statistics such as the total absolute point difference between the long term and short term ensemble averages, heart rate, activity rate, or the like in device memory upon completion of the ischemia diagnostic test.

In some embodiments the ischemia burden metric includes an indication of the certainty of the detection and/or the severity of the ischemia. In one embodiment for example, the degree by which the difference in absolute point differences exceeds the threshold for ischemia detection is mapped to a severity/likelihood index. In some embodiments, a low value for the severity/likelihood index indicates the threshold for detection was barely exceeded and high values indicate the threshold was exceeded by at least a predetermined percentage. In these embodiments the burden metric tracks the number of ischemia event detections and the severity level of each detected event.

The event log and/or the recorded electrogram exhibiting the ischemia may be downloaded at a later time to a clinician for analysis via an external programmer. The clinician is then able to use this information in making subsequent treatment decisions.

Ischemia is a condition resulting from insufficient blood flow through the heart muscle. Because myocardial perfusion occurs primarily during the diastolic phase, lower heart rates, which have a correspondingly longer diastolic phase, are conducive to increased perfusion while high heart rates have the potential of exacerbating an ischemic condition. Therefore, in some embodiments the microcontroller automatically adjusts the pacing mode or pacing parameters in response to the detection of an ischemic condition to ensure that the heart is not paced at a rate that might worsen the ischemic effects 480.

For instance, in one embodiment the microcontroller automatically switches to a non-tracking pacing mode in response to the detection of an ischemic condition. Alternatively, the microcontroller may adjust various pacing parameters in response to the detection of an ischemic condition. For example, in one embodiment the microcontroller automatically decreases the maximum tracking rate to limit the rate at which the ventricles can be paced regardless of the atrial rate to ensure that the heart is not paced at a rate that exacerbates the ischemic condition.

The microcontroller may also automatically adjust the maximum pacing rate during rate-adaptive pacing in response to the detection of cardiac ischemia. Typically, a rate responsive cardiac stimulation device increases its pacing rate (up to a maximum sensor rate) in response to increases in the patient's activity level. The rate of this change is referred to as the aggressiveness of the rate response.

However, in an ischemic state, the aggressiveness of the rate response may provide for a pacing rate that exacerbates the ischemic effects. Accordingly, in some embodiments of the present invention the microcontroller adaptively reduces the maximum sensor rate or increases the atrio-ventricular (AV) delay in response to the detection of an ischemic state.

In addition, in some embodiments, the implantable device forces the ventricular rate lower than the sinus rate through special pacing techniques such as the one described in commonly owned U.S. Pat. No. 6,377,852, entitled "Implantable Cardiac Stimulation Device And Method For Prolonging Atrial Refractoriness" by Bornzin, Sloman, Boileau and Florio, the content of which is incorporated herein by reference as if set forth in full. Conversely, when an ischemic state is no longer detected, the adapted variables are incrementally returned toward their original values. Accordingly, ischemia can be minimized while still maintaining the rate responsive features of the implantable cardiac stimulation device.

One of skill in the art will appreciate that the present invention is not limited to detecting ischemic events based solely upon the difference of a short term absolute point value for the short term ensemble average and a complex under test and a long term absolute point value for a long term ensemble average and a complex under test. Rather, in some embodiments an ischemic event can be detected through a direct comparison of the long term ensemble average and the short term ensemble average as updated for a predetermined number of test complexes.

In this embodiment the microcontroller updates the ensemble averages for the predetermined number of complexes and detects ischemia if the absolute point difference of the short term ensemble average and the long term ensemble average exceeds a threshold value. The threshold value may be programmed by the physician or automatically determined by the device.

One of skill in the art will further appreciate that the present invention is not limited to detecting ischemic events using the absolute point difference. Rather, the present invention generally utilizes morphology changes in the QRST segment and can therefore utilize any known technique for detecting changes in the long term and short term morphology of the QRST segment. For example, in some embodiment the microcontroller may compare the area under the test complex and ensemble averages to detect ischemia.

In addition, in some embodiments the microcontroller also utilizes changes in the paced evoked response, as reflected in the value of the paced depolarization integral, to verify the occurrence of an ischemic event. In these embodiments, the microcontroller calculates the paced depolarization integral for each paced ventricular evoked response. The microcontroller then compares the paced depolarization integral to a running average of previous PDI values (or against any suitable representation of nominal PDI values for the patient) to detect and evaluate recent changes in the IEGM complex. If the difference between the PDI values and the running average exceeds some predetermined threshold the occurrence of an ischemic event is verified.

In addition, in some embodiments of the present invention the implantable stimulation device may alert the patient of the detection of an ischemic condition so that the patient can take appropriate action such as taking medication, ceasing exertion, lying down, etc. The implantable device may utilize an audio or vibratory signal to alert the patient. Alternately, the device may telemeter an alert message to an external device which subsequently conveys the message to the patient or to an external monitoring center.

In addition, some embodiments of the present invention include the ability to implement a therapeutic action in response to the detection of an ischemic condition. For example, the microcontroller may initiate the infusion of a thrombolytic agent or anticoagulant agent in response to the detection of an ischemic event to prevent more serious medical complications.

The present invention can therefore be used to measure and track paced R wave, ST-segment and T wave changes associated with the occurrence of ischemia or as indication of physical abnormalities such as hypoglycemia or hyperglycemia or other conditions. For example, FIG. 5 graphically illustrates a typical pre-ischemic IEGM waveform 500 including the PDI integration area 510 for the paced evoked response. In this illustrative example, the IEGM analysis region 520 which is analyzed for morphological changes includes the majority of the S-T segment and the majority of the T wave.

In some embodiments of the present invention the microcontroller analyzes the morphology changes in the QRST complex not S-T segment shifts. In other embodiments a portion of the R wave is excluded from the IEGM comparison to eliminate potential errors introduced by the comparatively higher slew rates and amplitudes of the R wave. However, if the microcontroller utilizes a relatively high sampling rate and large dynamic range the entire R wave may be utilized to detect ischemic events.

Figure 5:
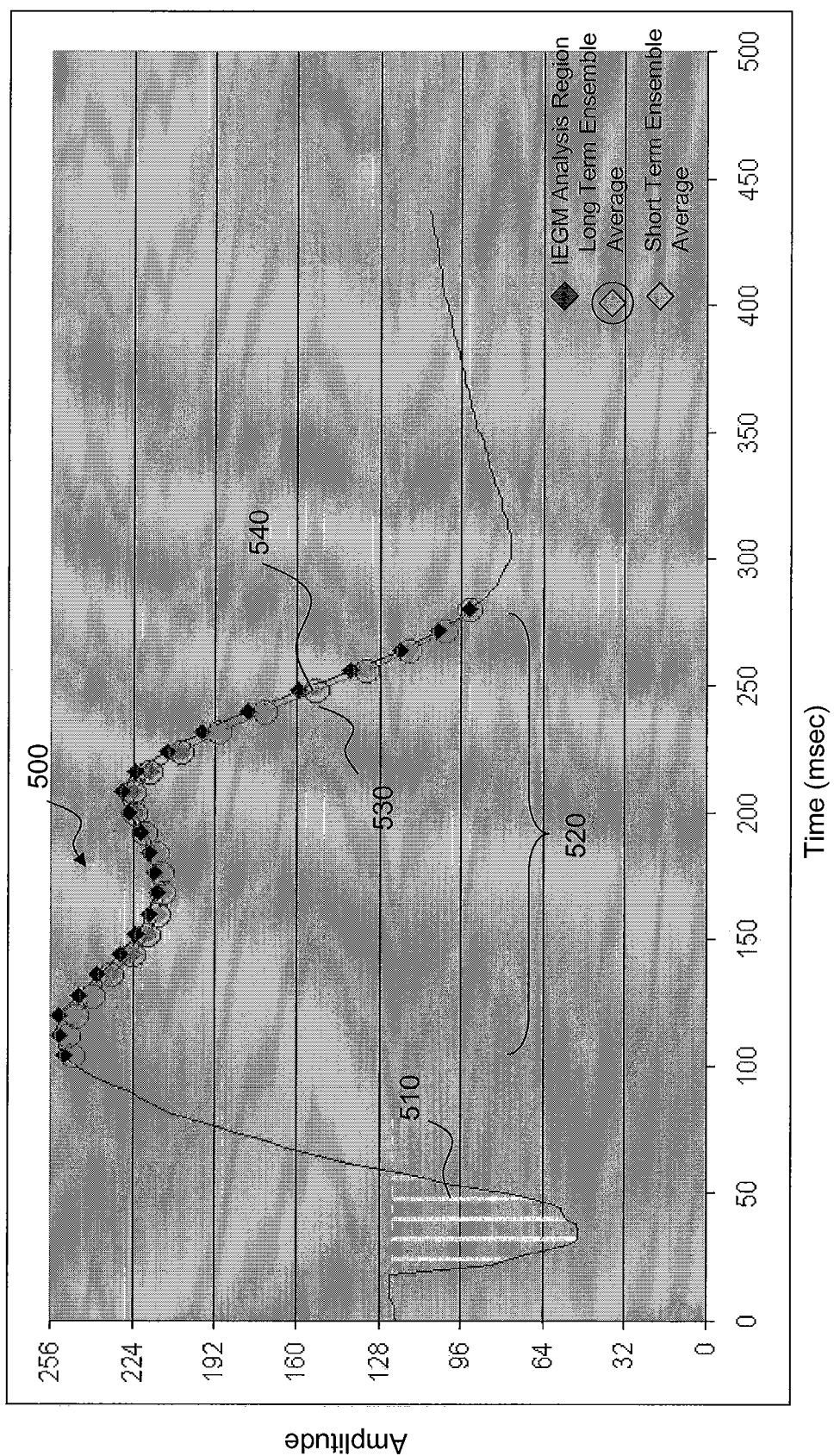
FIG. 5 graphically illustrates a pre-ischemic IEGM waveform with PDI integration area and long term and short term ensemble averages in accordance with one embodiment of the invention.

In the pre-ischemic waveform illustrated in FIG. 5, the long term ensemble average 530 and the short term ensemble average 540 closely overly each other and the test IEGM complex. Thus, in this example both ensemble averages have converged to the relatively constant and stable non-ischemic IEGM morphology.

Figure 6:
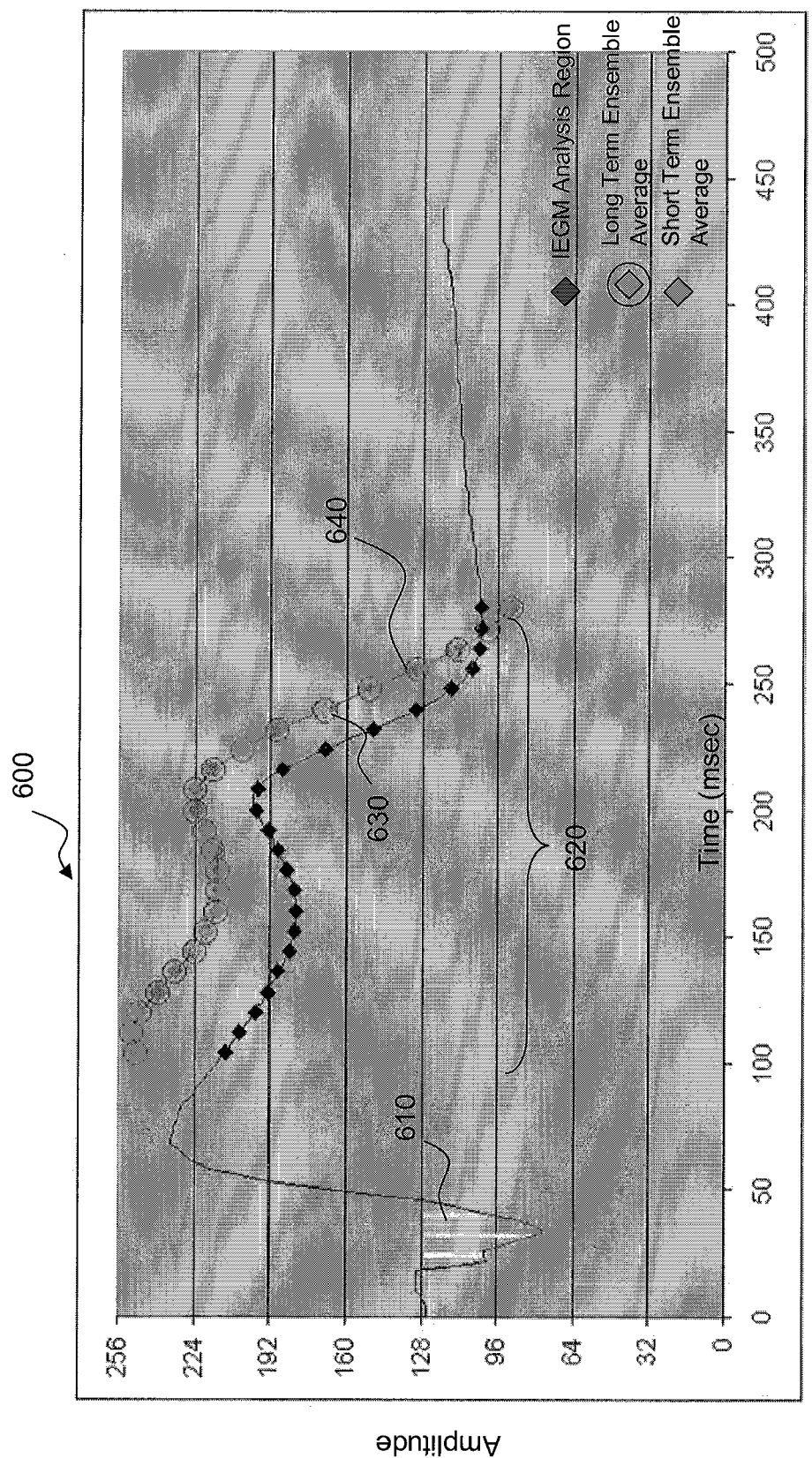
FIG. 6 graphically illustrates a pre-ischemic, fusion IEGM waveform with PDI integration area and long term and short term ensemble averages in accordance with one embodiment of the invention.

FIG. 6 graphically illustrates a typical non-ischemic, fusion IEGM waveform 600 including the PDI integration area 610 for the paced evoked response. In this illustrative example, the PDI integration area has changed in size and morphology as compared to the pre-ischemic waveform of FIG. 5 due to the fusion of the paced and intrinsic beats. The IEGM analysis region 620 which is analyzed for the morphological changes again includes the majority of the S-T segment and the majority of the T wave. The long term ensemble average 630 and the short term ensemble average 640 closely overly each other for the fusion waveform.

In the illustrated example, fusion beats occurred on a relatively rare basis. Therefore, in this instance both the short term and the long term ensemble average fail to converge to the fusion waveform 620 indicating that both the short term ensemble average and the long term ensemble average retained the typical non-ischemic, non-fusion IEGM morphology and a fusion beat is detected. In addition, the IEGM complex in this example does not trigger the detection of an ischemic event because the value of the short term ensemble average and the long term ensemble average are essentially the same. Therefore, the difference between the long term and short term absolute point differences for the complex under test would not exceed a typical ischemia detection threshold.

Figure 7:
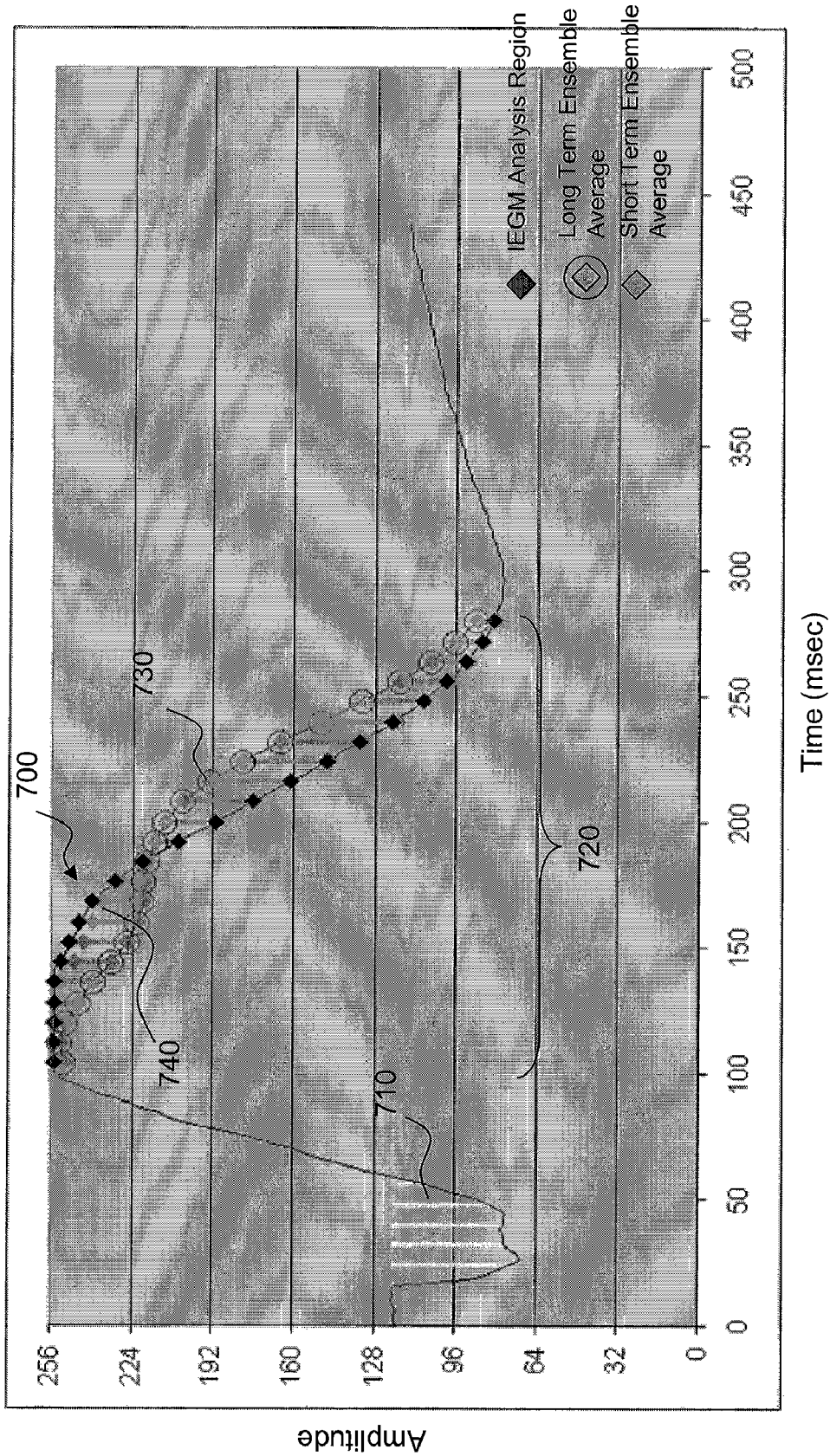
FIG. 7 graphically illustrates an ischemic, IEGM waveform with PDI integration area and long term and short term ensemble averages in accordance with one embodiment of the invention.

FIG. 7 graphically illustrates a typical ischemic IEGM waveform 700 including the PDI integration area 710 for the paced evoked response. In this illustrative example, the PDI integration area has again changed in size and morphology as compared to the pre-ischemic waveform of FIG. 5, due to the onset of ischemia.

The IEGM analysis region 720 which is analyzed for the morphological changes again includes the majority of the S-T segment and the majority of the T wave. The long term ensemble average 730 has again diverged from the IEGM complex under test 720 indicating that the long term ensemble average has retained most of the typical non-ischemic IEGM morphology. However, in this example, the values of the long term ensemble average 730 and the short term ensemble average 740 have also diverged as the short term average more quickly adapts to the altered morphology of the ischemic IEGM waveforms measured subsequent to the onset of ischemia.

Therefore, the difference of the absolute point difference for the long term and short term ensemble averages for the complex under test would exceed a typical ischemia detection threshold. The microcontroller therefore detects an ischemic event as a result of the difference between the long term and short term ensemble averages.

While the invention herein disclosed has been described by means of specific embodiments and applications thereof, numerous modifications and variations could be made thereto by those skilled in the art without departing from the scope of the invention set forth in the claims. For example, the methods or algorithms described in connection with the embodiments disclosed herein may be embodied directly in hardware, in a software module executed by a processor, or in a combination of the two.

A software module may reside in RAM memory, flash memory, ROM memory, EPROM memory, EEPROM memory, registers, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method, comprising:
   sensing a test IEGM waveform;
   sensing a plurality of IEGM waveforms;
   generating a long term ensemble average of the plurality of IEGM waveforms;
   generating a short term ensemble average of at least a portion of the plurality of IEGM waveforms;
   determining a short term absolute point difference as a function of a difference of an amplitude of the short term ensemble average and the test IEGM waveform at a plurality of sample points;
   determining a long term absolute point difference as a function of a difference of an amplitude of the long term ensemble average and the test IEGM waveform at a plurality of sample points; and
   detecting ischemia if a difference between the short term absolute point difference and the long term absolute point difference is greater than an ischemia detection threshold.

2. The method of claim 1 further comprising generating a baseline paced depolarization integral value for at least a portion of the plurality of IEGM waveforms and confirming the detection of ischemia if a difference between a value of a test paced depolarization integral for a test IEGM waveform and the value of the baseline paced depolarization integral exceeds a second ischemia detection threshold.

3. The method of claim 1 further comprising generating and storing an ischemia burden metric.

4. The method of claim 1 further comprising adjusting cardiac pacing parameters to increase heart perfusion in response to detection of ischemia.

5. The method of claim 1 further comprising notifying patient of detection of ischemia.

6. A medical device, comprising:
means for sensing IEGM waveforms and a test IEGM waveform;
means for generating a long term ensemble average of a plurality of the sensed IEGM waveform;
means for generating a short term ensemble average of at least a portion of the plurality of IEGM waveforms;
means for determining a short term absolute point difference as a function of a difference of an amplitude of the short term ensemble average and the test IEGM waveform at a plurality of sample points;
means for determining a long term absolute point difference as a function of a difference of an amplitude of the long term ensemble average and the test IEGM waveform at a plurality of sample points; and
means for detecting a ischemia if a difference between the short term absolute point difference and the long term absolute point difference is greater than an ischemia detection threshold.

7. The medical device of claim 6 further comprising means for generating a baseline paced depolarization integral value for at least a portion of the plurality of IEGM waveforms and confirming the detection of ischemia if a difference between a value of a test paced depolarization integral for a test IEGM waveform and the value of the baseline paced depolarization integral exceeds a second ischemia detection threshold.

8. The medical device of claim 6 further comprising means for tracking ischemia detection as a function of time and means for generating and storing an ischemia burden metric as a function of the detection of ischemia as a function of time.

9. The medical device of claim 6 further comprising means for adjusting cardiac pacing parameters to increase heart perfusion in response to detection of ischemia.

10. The medical device of claim 6 further comprising means for notifying a patient of detection of ischemia.

11. A medical device, comprising:
a pulse generator adapted to deliver a plurality of pacing pulses to a patient's heart;
a sensing circuit adapted to sense a plurality of baseline IEGM waveforms and a test IEGM waveform; and
a microcontroller adapted to determine a long term ensemble average of a plurality of baseline IEGM waveforms and to determine a short term ensemble average of at least a portion of the plurality of baseline IEGM waveforms,
the microcontroller being further adapted to determine a long term absolute point difference as a function of a difference between the long term ensemble average and the test IEGM waveform and a short term absolute point difference as a function of a difference between the short term ensemble average and the test IEGM waveform at a plurality of sample points and to detect ischemia if a difference between the short term absolute point difference and the long term absolute point difference is greater than an ischemia detection threshold.

12. The medical device of claim 11 wherein the microcontroller is further adapted to generate a baseline paced depolarization integral value for at least a portion of the plurality of IEGM waveforms and confirming the detection of ischemia if a difference between a value of a test paced depolarization integral for a test IEGM waveform and the value of the baseline paced depolarization integral exceeds a second ischemia detection threshold.

13. The medical device of claim 11 wherein the microcontroller is further adapted to adjust cardiac pacing parameters to increase heart perfusion in response to the detection of ischemia.

14. The medical device of claim 11 wherein the microcontroller is further adapted to generate an ischemia burden metric.

15. The medical device of claim 11 wherein the microcontroller is further adapted to notify a patient of detection of ischemia.

* * * * *

UNITED STATES PATENT AND TRADEMARK OFFICE
CERTIFICATE OF CORRECTION

PATENT NO. : 7,647,104 B1
APPLICATION NO. : 11/549517
DATED : January 12, 2010
INVENTOR(S) : Snell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 428 days.

Signed and Sealed this

Sixteenth Day of November, 2010

David J. Kappos
*Director of the United States Patent and Trademark Office*